(12) United States Patent
Lowe et al.

(10) Patent No.: US 6,583,333 B1
(45) Date of Patent: Jun. 24, 2003

(54) LYMPHOMA-SUSCEPTIBLE TRANSGENIC MICE AND METHODS FOR STUDYING DRUG SENSITIVITY OF LYMPHOMAS

(75) Inventors: Scott W. Lowe, Cold Spring Harbor, NY (US); Rachel R. Wallace-Brodeur, Huntington Station, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 09/076,776

(22) Filed: May 12, 1998

(51) Int. Cl.$^7$ .................. G01N 33/00; A01K 67/033; A01K 67/027; C12N 5/06; A61K 49/00
(52) U.S. Cl. .................. 800/3; 800/13; 800/14; 800/18; 435/325; 435/352; 435/354; 435/355; 424/9.1; 424/9.2
(58) Field of Search .................. 800/3, 18; 435/325, 435/352, 354, 355

(56) References Cited

U.S. PATENT DOCUMENTS

| | | | |
|---|---|---|---|
| 5,087,571 A | 2/1992 | Leder et al. | 435/354 |
| 5,175,383 A | 12/1992 | Leder et al. | 800/10 |
| 5,709,844 A | * 1/1998 | Arbeit et al. | 800/3 |

OTHER PUBLICATIONS

LA Donehower et al., Molecular Carcinogenesis, "Effects of Genetic Background on Tumorigenesis in p53–Deficient Mice," (1995), 14:16–22.*
D–H Cho et al., Journal of Biomedical Science,"IL–6 undergoes transition from in vitro autocine growth factor to in vivo growth inhibitor of B lymphoma cells," 1997,4/5, pp. 201–207.*
Jacks, T. et al., "Effects of an Rb mutation in the mouse," Nature, vol. 359, pp. 295–300, Sep. 24, 1992.
Strasser, A. et al., "Novel primitive lymphoid tumours induced in transgenic mice by cooperation between myc and bcl–2," Nature, vol. 348, pp. 331–333, Nov. 22, 1990.
Serrano, M. et al., "Role of the INK4a Locus in Tumor Suppression and Cell Mortality," Cell, vol. 85, pp. 27–37, Apr. 5, 1996.
Harris, A. W. et al., "The E$\mu$–myc Transgenic Mouse A Model for High–incidence Spontaneous Lymphoma and Leukemia of Early B Cells," J. Exp. Med., vol. 167, pp. 353–371, Feb. 1988.
Hsu, B. et al., "Evidence that c–myc mediated apoptosis does not require wild–type p53 during lymphomagenesis," Oncogene, vol. 11, pp. 175–179, 1995.
Langdon, W. Y. et al., "The c–myc Oncogene Perturbs B Lymphocyte Development in E$\mu$–myc Transgenic Mice," Cell, vol. 47, pp. 11–18, Oct. 10, 1986.
Samuelson, A. V. et al., "Selective induction of p53 and chemosensitivity in RB–deficient cells by E1A mutants unable to bind the RB–related proteins," Proc. Natl. Acad. Sci. USA, vol. 94, pp. 12094–12099, Oct. 1997.
Adams, J. M. et al., "The c–myc oncogene driven by immunoglobulin enhancers induces lymphoid malignancy in transgenic mice," Nature, vol. 318, pp. 533–538, Dec. 12, 1985.
Lowe, S. W. et al., "p53 is required for radiation–induced apoptosis in mouse thymocytes," Nature, vol. 362, pp. 847–849, Apr. 29, 1993.
Hermeking, H. et al., "Mediation of c–Myc–Induced Apoptosis by p53" Science, vol. 265, pp. 2091–2093, Sep. 30, 1994.
Donehower, L. A. et al., "Mice deficient for p53 are developmentally normal but susceptible to spontaneous tumours," Nature, vol. 356, pp. 215–221, Mar. 19, 1992.
Lowe, S. W. et al., "p53–Dependent Apoptosis Modulates the Cytotoxicity of Anticancer Agents," Cell, vol. 74, pp. 957–967, Sep. 24, 1993.
Lowe, S. W. et al., "p53 Status and the Efficacy of Cancer Therapy in Vivo," Science, vol. 266, pp. 807–810, Nov. 4, 1994.
Barrington, R. E. et al., "A Farnesyltransferase Inhibitor Induces Tumor Regression in Transgenic Mice Harboring Multiple Oncogenic Mutations by Mediating Alterations in Both Cell Cycle Control and Apoptosis," Molecular and Cellular Biology, vol. 18, No. 1, pp. 85–92, Jan. 1998.
Elson, A. et al., "The MMTV/c–myc transgene and p53 null alleles collaborate to induce T–cell lymphomas, but not mammary carcinomas in transgenic mice," Oncogene, vol. 11, pp. 181–190, 1995.

* cited by examiner

Primary Examiner—Anne-Marie Falk
(74) Attorney, Agent, or Firm—Hamilton, Brook, Smith & Reynolds, P.C.

(57) ABSTRACT

A mouse expressing myc in B cells, because of defective function of one or more tumor suppressor genes, is useful for the testing of anti-lymphoma agents and for the testing of genes which may have an effect on the apoptotic pathway. Preferred embodiments include mice of genotypes E$\mu$-myc/p53$^{+/-}$, E$\mu$-myc/Rb$^{+/-}$ and E$\mu$-myc/p16$^{+/-}$, and cells derived from lymphomas arising in these mice, wherein the cells may have undergone further genetic alteration. Mouse strains, lymphoma cells and cell lines of the invention can be used in methods to discover new anti-lymphoma agents, methods to characterize tumors, and to characterize genes which may affect the development of resistance to anti-tumor agents. Such methods are also part of the invention.

10 Claims, 6 Drawing Sheets

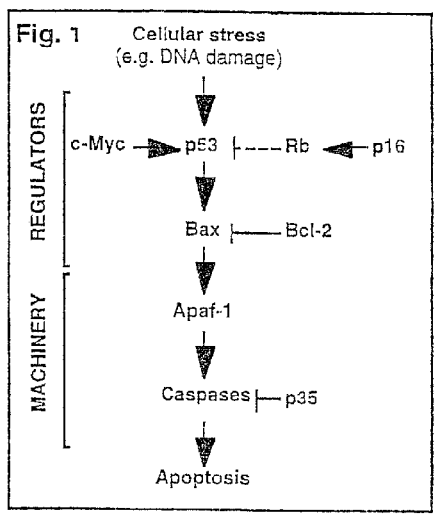
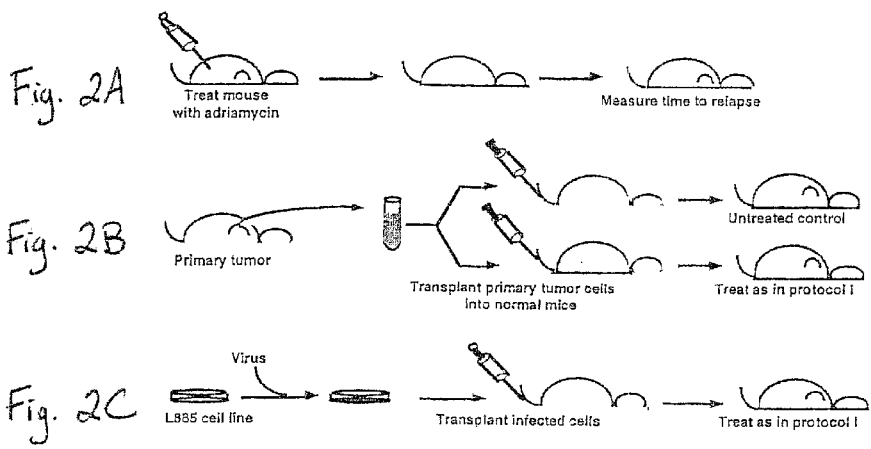
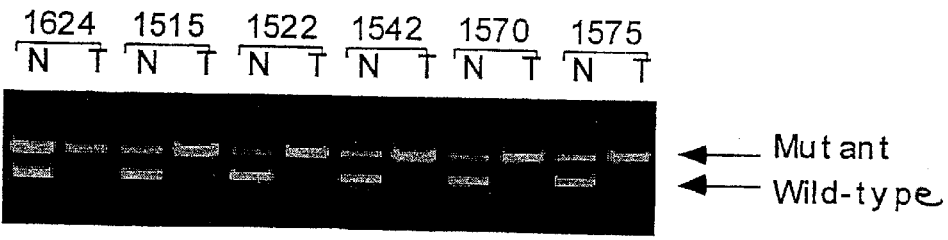
Fig. 3

Primary vs Transplanted tumor response to ADR

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (xi) SEQUENCE DESCRIPTION: SEQ ID NO:1:

CAGCTGGCGT AATAGCGAAG AG                            22

(2) INFORMATION FOR SEQ ID NO:2:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (xi) SEQUENCE DESCRIPTION: SEQ ID NO:2:

CTGTGACTGG TGAGTACTCA ACC                                    23

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:3:

TATACTCAGA GCCGGCCT                                          18

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:4:

ACAGCGTGGT GGTACCTTAT                                        20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:5:

TCCTCGTGCT TTACGGTATC                                        20

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:6:

ATGATGATGG GCAACGTTC                                         19

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:7:

CAAATATCGC ACGATGTC                                          18

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:8:

```
GGGCGCCCGG TTCTTTT                                              17
```

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:9:

```
CCAGCCGGCC ACAGTCG                                              17
```

LYMPHOMA-SUSCEPTIBLE TRANSGENIC MICE AND METHODS FOR STUDYING DRUG SENSITIVITY OF LYMPHOMAS

GOVERNMENT SUPPORT

This invention was made, in part, with support under Grant No. CA13106 awarded by the National Institutes of Health. The U.S. Government has certain rights in the invention.

BACKGROUND OF THE INVENTION

Tumor suppressors are generally identified as genes in which loss of function causes tumor formation, either as seen by transformation of cells in culture, or by association of mutations with tumors in animals. The usual normal function of these genes is to impose some constraint on the cell cycle or cell growth. In certain cancers, patients develop tumors which have mutations in both alleles of the tumor suppressor gene. p53, Rb and p16 are among the best characterized of the tumor suppressor genes.

In vitro analysis of human tumor cell lines from some tumor types show a correlation between p53 mutations and resistance to treatment. Burkitt's lymphoma cell lines with mutant p53 are more resistant to a variety of treatments when compared to those with wild type p53 (Fan S., et al., Cancer Res. 54,5824–30, 1994). Consistent with in vitro studies, p53 status is linked to drug resistance in several tumor types. Perhaps the most striking examples occur in lymphoid malignancies, including non-Hodgkin's lymphoma, acute myeloid leukemia, myelodysplastic syndrome, and chronic lymphocytic leukemia (Wattel, E., et al., *Blood* 84, 3148–57 1994; Wilson, W. H., et al., *Blood* 89, 601–9 1997). In these tumor types, p53 mutations are rare but generally associated with disease progression and poor prognosis. When patients are classified by p53 status, tumor response (i.e. remission vs. nonresponsive), and survival, patients with p53 mutations are remarkably resistant to therapy and display very short survival times. In this regard, a particularly informative tumor type is acute lymphoblastic leukemia. Here, p53 mutations in primary tumors are exceedingly rare, and most patients typically respond to therapy. However, a subfraction of patients relapse, and approximately 30% of relapsed tumors harbor mutant p53. Moreover, patients with p53 mutant tumors are less likely to enter a second remission compared to patients with relapsed tumors harboring wild-type p53 (Diccianni, M. B., et al., *Blood* 84, 3105–12 1994; Hsiao, M. H., et al., *Blood* 83, 2922–30 1994).

It is now known that most anticancer agents induce apoptosis, a genetically-regulated form of cell death (reviewed in Kerr, J. F. R. et al., *Cancer* 73:2013–2026, 1994). Since drugs with distinct primary targets can induce apoptosis through similar mechanisms, mutations in apoptotic programs can produce multiple drug resistance (Dive, C., and Hickman, J. A., *Br. J. Cancer* 64:192–196, 1991). These observations raise the possibility that the chemosensitivity of human tumors is determined, in part, by the combined effects of oncogenic mutations on apoptosis (Lowe, S. W. et al., *Cell* 74:957–967, 1993).

Considerable progress has been made in identifying components of apoptotic programs, although the interaction between these components and their precise modes of action remain elusive. A schematic diagram that illustrates a loose hierarchy of an apoptotic "pathway' is shown in FIG. 1.

Resistance to cytotoxic agents used in cancer therapy remains a major obstacle in the treatment of human malignancies, including leukemia and lymphoma. Since most anticancer agents were discovered through empirical screens, efforts to overcome resistance are hindered by our limited understanding of why these agents are ever effective. The role of apoptosis in malignancy provides a new explanation for drug sensitivity and resistance. This view suggests that responsive tumors must readily undergo apoptosis in response to cytotoxic agents and that resistant tumors may have acquired mutations that suppress apoptosis. Also, the fact that apoptosis is controlled by genes raises the prospect that the problem of drug sensitivity and resistance will be amenable to molecular biology.

One of the difficulties in identifying determinants of drug cytotoxicity in vivo is the limited availability of appropriate material. Human tumor lines grown as xenographs are unphysiological, and the wide variation between human individuals, not to mention treatment protocols, makes clinical studies difficult. Consequently, oncologists are forced to perform correlative studies with a limited number of highly dissimilar samples, often leading to confusing results.

SUMMARY OF THE INVENTION

The invention encompasses a mouse which expresses the oncogene myc in its B cells, and is thereby susceptible to lymphoma. The expression of myc in B cells can result from a number of genetic events, either natural or created by man. Preferred embodiments include a mouse of genotype Eµ-myc/mutated tumor suppressor gene, such as Eµ-myc/p53$^{+/-}$, Eµ-myc/Rb$^{+/-}$, and Eµ-myc/p16$^{+/-}$.

The invention also encompasses cell lines that can be cultured from lymphoma cells arising in a mouse of the invention, preferably a mouse of genotype Eµ-myc/p53$^{+/-}$, Eµ-myc/Rb$^{+/-}$, or Eµ-myc/p16$^{+/-}$. The cells of these cultured cell lines can have genetic changes beyond those in non-lymphoma cells of the mouse from which they are derived.

The invention also includes methods for testing a lymphoma, either a primary tumor or one that has recurred after one or more remissions, for sensitivity to an anti-tumor treatment, by giving the treatment to a mouse of the invention, such as an Eµ-myc/mutated tumor suppressor gene mouse, and monitoring the mouse for a response to the treatment, such as remission from the lymphoma. A treatment can be tested for its effectiveness against lymphoma by the use of similar steps.

Further methods employ the cell lines of the invention. For example, Eµ-myc/mutated tumor suppressor gene lymphoma cells can be cultured in vitro, given a treatment, and monitored for slowed or stopped growth relative to an untreated or sham-treated population of the same cell type. A further test of a treatment involves transplanting lymphoma cells from an Eµ-myc/mutated tumor suppressor gene mouse into a mouse of a type which normally does not develop lymphoma (preferably an immunocompetent mouse), administering the treatment to the recipient mouse after it develops lymphoma, and monitoring the treated recipient mouse for remission. A transplanted, recipient mouse which does not receive the treatment can serve as a control for comparison.

The invention further encompasses a method to assess an effect of a gene on the response of a lymphoma to a treatment, using a cell line derived from the lymphoma. A gene can be introduced into a population of cells of the cell line to make "test" cells, and another population of cells of the same cell line can be used as controls (e.g., left unaltered, transfected with control virus not bearing gene, transformed with control vector not bearing gene). Test or control cells can be introduced into one or more mice, and the two groups of mice can be given an identical treatment and monitored for remission.

BRIEF DESCRIPTION OF THE DRAWINGS

FIG. 1 is a diagram illustrating a general hierarchy and the interactions of genes involved in an apoptotic "pathway."

FIGS. 2A–2C are diagrams illustrating three different protocols used to test the response of myc-induced lymphomas to drug therapy. FIG. 2A illustrates Protocol 1 in which animals bearing palpable tumors are given an anti-lymphoma treatment and monitored for remission and relapse by palpation and by blood smears. FIG. 2B illustrates Protocol 2 in which lymphoma cells are harvested upon tumor presentation from an Eµ-myc transgenic animal and cells are immediately transplanted into multiple recipient animals by tail vein injection. Tumors are allowed to form, and treatment proceeds as in FIG. 2A (Protocol 1). FIG. 2C illustrates Protocol 3, in which a gene is introduced into a lymphoma cell line by viral transfection. Transfected lymphoma cells are transplanted into recipient mice. After developing lymphomas, the recipient mice are treated as in Protocol 1.

FIG. 3 is a scan of an agarose gel after electrophoresis of the products of a PCR amplification of a portion of the p53 gene in genomic DNA, to detect the presence of two mutant alleles, two wild type alleles or one allele of each type. See Example 4 and Example 1.

FIG. 2B) as monitored by palpable tumors. The solid line indicates the response of primary tumors; the dashed line indicates the response of transplanted tumors as percentage of mice that are free of tumors. See Example 6.

DETAILED DESCRIPTION OF THE INVENTION

Figure 4:
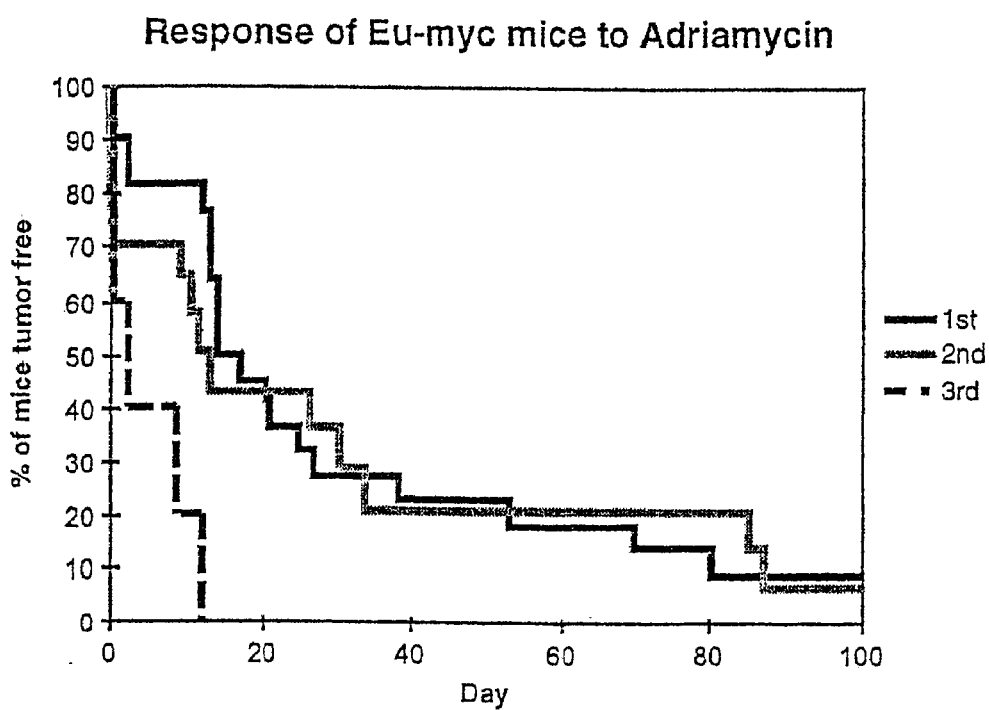
FIG. 4 is a graph illustrating the response of Eµ-myc mice to adriamycin (ADR), where the black solid line shows the percentage of tumor-free mice after the first round of treatment, the grey line indicates the percentage of tumor-free mice after the second round of treatment after a first relapse, and the dashed line indicates the percentage of tumor-free mice after the third round of treatment after a second relapse. Treatments were as in FIG. 2A, Protocol 1. See Example 5.

It is an object of the invention to provide a mouse which expresses myc in B cells, wherein myc expression is manifested by lymphoma. Such mice are characterized by having B cells that harbor mutations affecting the function of one or more so-called tumor suppressor genes, and that express myc, with the result that the mice develop lymphomas. Such mice can be of genotype Eµ-myc/mutant tumor suppressor gene, for example Eµ-myc/p53$^{+/-}$, Eµ-myc/Rb$^{+/-}$ or Eµ-myc/p16$^{+/-}$. Such mice can also be of a genotype which produces a phenotype mimicking that resulting from an Eµ-myc/mutant tumor suppressor gene genotype.

The invention comprises strains of mice that may be syngeneic, harboring a combination of genes: (1) a myc gene and (2) a mutant tumor suppressor gene (one or more mutant alleles) which results in lack of a function which in the wild type causes suppression of myc-induced tumor formation. The myc gene can be under the control of a promoter/enhancer region specific to B cells, such that the myc gene is specifically expressed in B cells, for example Eµ-myc (Adams, J. M. et al., *Nature* 318:533–538, 1985).

Eµ-myc/tumor suppressor gene mutation mice are mice having the genotype of the myc oncogene, under the control of the EA IgH enhancer, in combination with a tumor suppressor gene mutation whose presence results in an increase in the probability of the development of tumors in an animal or human (relative to the probability of tumor development in animals in which wild type alleles of the suppressor gene are present). The myc gene can be one as described in Harris, A. W., *J. Exp. Med.* 167:353–371 (1988) or the allelle described by Langdon, W. Y. et al., *Cell* 47:11–18 (1986), for example. The myc gene can also be a naturally-occurring gene, either cellular or viral, a natural variant or an artificially altered variant of myc.

The p53 gene can be a mutant allele described by Donehower, L. A. et al., 356:215–221 (1992) or as described by Jacks, T. et al., *Curr. Biol.* 4:1–7 (1994) or Purdie, C. A. et al. *Oncogene* 9:603–609 (1994). The p53 allele can also be one made by various methods of mutagenesis. Loss of p53 (or of another tumor suppressor gene) function can occur, for instance, through point mutation, allelic loss, rearrangements, and intragenic deletions.

The Rb gene can be one described in Jacks, T. et al., Nature 359:295–300 (1992), in Clarke, A. R. et al., Nature 359:328–330, 1992, or in Lee, E. Y. et al, Nature 359:288–294, 1992. The Rb gene can also be one that is isolated from a source in nature or produced in vitro by methods of genetic manipulation.

The p16 gene can be the allele described by Serrano, M. et al., Cell 85:27–37, 1996, or can be other alleles found in nature or altered by in vitro or in vivo manipulations.

Other mutated tumor suppressor genes can be used in combination with E$\mu$-myc in genetically engineered mice. For example, mutated caspase genes or mutated genes of the bcl-2 family (e.g., bax, bak, bik, bad) can be used.

Preferred embodiments of mice which express myc and are defective in tumor suppressor function are those mice having the genotype E$\mu$-myc/p53$^{+/-}$, E$\mu$-myc/Rb$^{+/-}$ or E$\mu$-myc/p16$^{+/-}$.

E$\mu$-myc/tumor suppressor gene mutation mice can be made by matings to take advantage of existing mutations, as illustrated in the Examples, or they can be made in a number of other ways. For example, it is possible to start with a mouse strain that harbors a mutation in a tumor suppressor gene, and by known methods of producing transgenic animals, introduce the E$\mu$-myc transgene into the genome, either by introducing the transgene into a fertilized ovum, using a c-myc vector construct such as the one described by Adams (Adams, J. M. et al., Nature 318:533–538, 1985) by the method of Wagner et al., U.S. Pat. No. 4,873,191 (1989), or by introducing the transgene into embryonic stem (ES) cells (see, for example, Capecchi, M. R., Science 244:1288–1292, 1989).

Where embryonic stem cells are used, the tumor suppressor gene can be specifically inactivated in cultured embryonic stem cells. For instance, a normal gene can be replaced with a copy of itself that contains a bacterial antibiotic resistance gene, such as neo. The neo gene not only inactivates the target gene, but also allows identification of cells that have taken up the engineered gene. The embryonic stem cells are then injected into mouse embryos, where they have the potential to develop into all the different mouse cell types. The resulting animals are then bred, and those whose germ cells are derived from the ES cells pass the inactivated gene to their progeny.

Further, alternative methods are available to produce conditional knockouts of the tumor suppressor gene of interest, or tissue specific knockouts.

The bacteriophage P1 Cre-loxP recombination system is capable of mediating loxP site-specific recombination in both ES cells and transgenic mice. The site-specific recombinase Cre can also be used in a predefined cell lineage or at a certain stage of development. See, for example, Gu, H. et al., Science 265:103–106, 1994, in which a DNA polymerase $\beta$ gene segment was deleted from T cells; see also Tsien, J. Z. et al., Cell 87:1317–1326, 1996, in which Cre/loxP recombination was restricted to cells in the mouse forebrain.) The impact of the mutation on these cells can then be analyzed.

The Cre recombinase catalyzes recombination between 34 bp loxP recognition sequences (Sauer, B. and Henderson, N., Proc. Natl. Acad. Sci. USA 85:5166–5170, 1988). The loxP sequences can be inserted into the genome of embryonic stem cells by homologous recombination such that they flank one or more exons of a gene of interest (making a "floxed" gene). It is crucial that the insertions do not interfere with normal expression of the gene. Mice homozygous for the floxed gene are generated from these embryonic stem cells by conventional techniques and are crossed to a second mouse that harbors a Cre transgene under the control of a tissue type- or cell type-specific transcriptional promoter. In progeny that are homozygous for the floxed gene and that carry the Cre transgene, the floxed gene will be deleted by Cre/loxP recombination, but only in those cell types in which the Cre gene-associated promoter is active.

A myc transgene can be delivered selectively into B cells in culture by methods for transfection, or by infection with a retrovirus which expresses myc under the control of a retroviral promoter. See, Pear, W. S. et al., J. Exp. Med. 183:2283–2291, 1996, for an example of retroviral transduction used to induce clonal leukemias.

Proteins which act to have the effect of mimicking the phenotype caused by tumor suppressor mutations can also be used to achieve the same effect as knockouts in tumor suppressor genes.

A dominant negative mutant can be used to achieve loss of function of a tumor suppressor gene, instead of using a tumor suppressor knockout. See, for example the description of the mutant Val-135 p53 allele in Harvey, M. et al., Nat. Genet. 9:305–311, 1995. For example, a transgenic E$\mu$-myc mouse which expresses a dominant negative p53 allele specifically in B cells can be made by a cross of an E$\mu$-myc mouse to a mouse having a dominant negative p53 gene under the control of a B-cell specific promoter, such as the IgH enhancer E$\mu$. A cell line expressing E$\mu$-myc and a dominant negative p53 can be made by introducing a dominant negative p53 gene into an E$\mu$-myc/p53$^+$ lymphoma cell line (e.g., by a retroviral construct, transformation, etc.).

The R24C mutation in the gene encoding cyclin-dependent kinase 4 (CDK4) has been found to prevent binding of the CDK4 inhibitor (and tumor suppressor) p16 (Wölfel, T. et al., Science 269:1281–1284 (1995)). As an alternative to an E$\mu$-myc/p16 (knockout) mouse, a transgenic mouse can be made in which CDK4-R24C is expressed, thereby producing the phenotype of an E$\mu$-myc/p16$^{-/-}$ mouse.

Expression in E$\mu$-myc mice of viral proteins that bind the Rb gene product and inactivate its function (e.g., human papilloma virus-16 E7 and adenovirus E1A) can be used to produce an E$\mu$-myc/Rb$^{-/-}$ phenotype. See, regarding adenovirus E1A protein, Whyte, P. et al., Nature 334:124–129, 1988. For the human papilloma virus-16 E7 oncoprotein, see Dyson, N. et al., Science 243:934–937, 1989.

Testing to identify the p53, Rb and p16 mutant or wild type alleles, or for the identification of other alleles, can be done by PCR on isolated genomic DNA, using appropriate primers, or by Southern blots using appropriate hybridization probes, by a combination of these procedures, or by other methods. For instance, hybridization probes to distinguish the p16 alleles (by detection of the insertion of the NEO cassette) have been published in Serrano, M. et al., Cell 85:27–37 (1996).

It is also an object of the invention to provide cell lines that are derived from lymphomas arising in E$\mu$-myc/mutant suppressor gene mice or in mice which by a different genotype mimic the phenotype of E$\mu$-myc/mutant suppressor gene mice. For example, cell lines of the invention can be stably dividing cells that grow in cell culture conditions, arising from mouse strains of the invention. Preferred genotypes of cell lines are E$\mu$-myc/p53$^{-/-}$ (e.g., cell line L1624), Eμ-myc/Rb$^{+/-}$ (e.g. cell line L1790) and Eμ-myc/p16$^{-/-}$ (e.g., cell line L1213). Cell lines can be made by using feeder layers of cells, as in the method described in Example 7, or by culturing the cells in a variety of media, including chemically defined media, without feeder layers.

An Eμ-myc/tumor suppressor gene mutation transgenic mouse strain provides a useful model for studying apoptosis and cancer therapy, since: (i) tumor burden can be monitored externally by lymph node palpation and often by blood smears; (ii) lymphomas are detectable long before the animals die, so animals can be treated while otherwise healthy, (iii) large numbers of tumor cells can be isolated from mice undergoing therapy or treatment, (iv) therapy is performed in immunocompetent mice, and (v) lymphoma cells readily adapt to culture and/or can be transplanted into syngeneic mice.

A lymphoma arising in a mouse of a specific strain described herein can be tested for sensitivity to a treatment, by administering the treatment to the mouse (designated a "test" mouse), and monitoring the mouse for a decrease in signs of the lymphoma (remission). Full remission is a state of normalcy of the mouse in which no lymphoma can be detected by palpation, and white blood cell counts are indistinguishable (not statistically significantly different) from those of healthy mice. Sensitivity of a lymphoma to a treatment can be proportional to the length of time until relapse. An appropriate control mouse is one which is genetically identical or very similar, and which has been maintained under the same conditions as the test mouse, except that no treatment has been given.

The treatment to be tested can be one or more substances, for example, a known anti-cancer agent, such as adriamycin, cylophosphamide, prednisone, vincristine or a radioactive source. The substance can be administered preferably by intraperitoneal injection in a pharmaceutically acceptable vehicle, but also by other vehicles and routes, for example, orally, intranasally, by inhalation, intramuscular injection, hypodermic injection, intravenous injection or by surgical implantation, in topical creams, transdermal patches and the like, all optionally with pharmaceutically compatible carriers and solvents. The treatment can also be exposure to various kinds of energy or particles, such as gamma-irradiation, or can be a combination of approaches. In some cases, the treatment can also be administration of one or more substances or exposure to conditions, or a combination of both, wherein the effects of the treatment as anti-cancer therapy are unknown.

Another embodiment of the invention is a further method for testing a lymphoma arising from an Eμ-myc/tumor suppressor gene mutation lymphoma for sensitivity to a treatment. Lymphoma cells are cultured in vitro, a treatment is administered to the cells (e.g., a drug is contacted with the cells), and the cells can be monitored for growth (e.g., by observing cell number, confluence in flasks, staining to distinguish viable from nonviable cells). A failure to increase in viable cell number, a slower rate of increase in cell number, or a decline in viable cell number, compared to cells which have been left untreated, or which have been mock-treated, is an indication of sensitivity to the treatment.

A further embodiment of the invention is a method employing secondary tumors arising from transplanted primary tumor cells. In this way, a statistically significant number of mice with the same lymphoma can be studied for their response to a regimen of therapy. One or more tumors arising in a Eμ-myc/tumor suppressor gene mutation mouse can be harvested from an animal and transplanted into recipient mice by a suitable method, such as by tail vein injection. After a period of time, lymphomas arise in the recipient mice. A treatment is then administered to one population of recipient mice which have developed tumors (making a "treated" population). A second population of recipient mice can serve as controls and remain untreated or be sham-treated. Thereafter, the treated population of mice is monitored for remission (ordinarily, by palpation for tumors). Remissions among the treated population indicates sensitivity of the lymphomas of the Eμ-myc/tumor suppressor gene mutation mice to the administered treatment.

A further embodiment of the invention is a test for the effect of a gene on sensitivity of a lymphoma to a treatment (e.g., anti-cancer drug). In one embodiment, a cell line can be produced from a lymphoma described herein. A gene to be tested for its effect on the sensitivity to a treatment of the lymphoma is introduced into cells of the cell line, such that the cells produce the gene product.

Introduction of the gene can be, for instance, by transformation, such as by electroporation, by calcium phosphate, DEAE-dextran, or by liposomes, using a vector which has been constructed to have an insertion of the gene. See Ausubel, F. M. et al, *Current Protocols in Molecular Biology*, chapter 9, containing supplements through Supplement 40, Fall, 1997, John Wiley & Sons, New York.

The introduction of a gene of interest can also be accomplished by viral infection, for example, by a retrovirus. Retroviral gene transfer has been used successfully to introduce genes into whole cell populations, thereby eliminating problems associated with clonal variation (McCurrach, M. E. et al., *Proc. Natl. Acad. Sci. USA* 94:2345–2349, 1997; Samuelson, A. V. and Lowe, S. W., *Proc. Natl. Acad. Sci. USA*:12094–12099, 1997; Serrano, M. et al., *Cell* 85:27037, 1997).

Cells so altered or transformed by the introduced gene, or unaltered cells, ["unaltered" including cells which have been transformed with a control vector, transfected with control DNA, or infected with a control virus (control constructs not carrying the gene of interest)], can be introduced into immunocompetent recipient mice ("test" mice receiving the gene and "control" mice not receiving the gene). Cells can be introduced by injection, for example, by injection into the tail vein of the mice. Lymphomas are allowed to form in both the test and control mice, and both test and control mice are monitored for the development of lymphomas. Both groups of mice are administered a treatment, preferably a drug given at a (C) STRANDEDNESS: single (D) TOPOLOGY: linear (xi) SEQUENCE DESCRIPTION: SEQ ID NO:9:

CCAGCCGGCC ACAGTCG 17 dose with a known anti-tumor effect, and monitored for remission. A difference in the frequency of remissions in the test mice compared to that of the control mice (remissions are not anticipated in control mice) indicates an effect of the gene on the response of the lymphoma to the treatment.

This method can determine what the response of an animal would be to the same therapy, with and without the gene. Thus, genes that are important to drug sensitivity of a lymphoma can be identified.

Animal models provide a useful alternative to studies in humans and to human tumor cell lines grown as xenographs, since large numbers of genetically-identical individuals can be treated with identical regimens, and experimental strategies are not limited by the same ethical considerations applied to humans. Moreover, the ability to introduce oncogenic mutations into the mouse germline increases the power of mouse models.

The invention described herein exploits mouse models to generate tumors with specific genetic alterations, allowing the production of useful tools for future drug discovery programs applicable to human lymphomas. By understanding the regulation and execution of apoptosis in tumor cells it may be possible to selectively increase the chemosensitivity of tumor cells, or to develop novel therapies to activate apoptosis more directly. Cell lines that recapitulate the behavior of spontaneous Eµ-myc lymphomas allow gene transfer studies in vitro and an evaluation of the impact of the gene on lymphomas produced in syngeneic recipients.

The present invention will now be illustrated by the following Examples, which are not intended to be limiting in any way.

EXAMPLES

Example 1

Producing Eµ-myc/p53$^{+/-}$ Mice

Eµ-myc transgenic mice (Harris, A. W., *J. Exp. Med.* 167:353–371, 1988) were allowed to mate with mice that were either heterozygous or homozygous for a mutant tumor suppressor gene p53 (Jacks, T. et al., *Curr. Biol.* 4:1–7, 1994). Progeny of the mated mice were tested for the Eµ-myc/p53$^{+/-}$ genotype by testing DNA purified from a small segment of tail, using PCR to detect the Eµ-myc transgene, as well as the wild type and mutant allele of p53.

Mouse tail DNA was prepared as follows. One cm or less of the tip of a mouse tail was cut off. 500 µl of lysis buffer (lysis buffer is 200 mM NaCl, 100 mM Tris-HCl, pH 8.5, 5 mM etheylenediaminetetraacetic acid (EDTA) and 0.2% sodium dodecyl sulfate) and 50 µl of 20 mg/ml Proteinase K were added to the segment of mouse tail in a centrifuge tube, and incubated overnight at 55° C. Centrifuge tubes of lysed tail material were centrifuged at 14,000 rpm for 10 minutes to pellet the hair and other insoluble material. The supernatant was transferred to a new tube. 500 µl of isopropanol were added to precipitate the DNA. The DNA was lifted out of the tubes with a pipette tip and resuspended in 200 µl of 0.1–0.25x TE, and stored at 4° C. DNA was not used in PCR for at least 24 hours.

Primers used for PCR to detect Eµ-myc as described by Harris are shown below:

| pUC-1 5'-CAG CTG GCG TAA TAG CGA AGA G | (SEQ ID no: 1) |
|---|---|
| pUC-2 5'-CTG TGA CTG GTG AGT ACT CAA CC | (SEQ ID no: 2) |

The reaction mix for PCR contained template DNA as prepared above, 0.48 µM for each primer, 20 µM mixed dNTPs, and 0.5 units of Taq DNA polymerase in a buffer consisting of 500 mM KCl, 200 mM Tris, pH 8.6, 10 mM MgCl$_2$, and 0.1% gelatin, in a volume of 25 µl.

PCR was done for an initial 94° C. for 5 minutes, then 25 cycles of 94° C. for 1 minute, 64° C. for 1 minute, 72° C. for 1.5 minutes, then a final 5 minutes of 72° C.

To identify the p53 alleles, PCR was done using the primers below, which produce fragments of different sizes from the wild type and mutant p53 alleles when they are used as template DNA. The wild type allele yields a fragment of about 375 nucleotides and the mutant allele yields a fragment of about 575 nucleotides.

| X7: 5'-TAT ACT CAG AGC CGG CCT | (SEQ ID no: 3) |
|---|---|
| X6.5: 5'-ACA GCG TGG TGG TAC CTT AT | (SEQ ID no: 4) |
| NEO: 5'-TCC TCG TGC TTT ACG GTA TC | (SEQ ID no: 5) |

The following were combined for PCR (volumes in µl):

1 template DNA
2.0 10X buffer as supplied by Perkin Elmer
2.0 2 mM dNTPs
0.4 X7 primer (20 µM)
0.15 X6.5 primer (20 µM)
0.35 NEO primer (20 µM)
0.1 Taq polymerase (0.5 units)

deionized water to a final volume of 20 µl The above reaction tubes were subjected to cycles of heating and cooling with a thermal cycler, using the following program: an initial 94° C. for 4 minutes, 30 cycles of (94° C. for 30 seconds, 62° C. for 1 minute, 72° C. for 1 minute), then 72° C. for 5 minutes.

Example 2

Producing Eµ-myc/Rb$^{+/-}$ Mice

Eµ-myc transgenic mice (Harris, A. W., *J. Exp. Med.* 167:353–371, 1988) were allowed to mate with mice heterozygous for tumor suppressor gene mutation Rb (Jacks, T. et al., *Nature* 359:295–300, 1992). Progeny of the mated mice were tested for the Eµ-myc/Rb$^{+/-}$ genotype by testing DNA purified from a small segment of tail, using PCR to detect the Eµ-myc transgene. The Rb$^{-/-}$ genotype was confirmed by testing tail DNA by PCR, using methods and primers published in Jacks, T. et al., *Nature* 359:295–300, 1992.

Example 3

Producing Eµ-myc/p16$^{+/-}$ Mice

Eµ-myc transgenic mice (Harris, A. W., *J. Exp. Med.* 167:353–371, 1988) were mated with mice that were heterozygous or homozygous for tumor suppressor gene mutation p16 (Serrano, M. et al., *Cell* 85:27–37, 1996). Progeny of the mated mice were tested for the Eµ-myc/p16$^{+/-}$ genotype by testing DNA purified from a small segment of tail, using PCR to detect the Eµ-myc transgene. Primers used for PCR to detect Eµ-myc were pUC-1 and pUC-2, described in Example 1. The p16$^{+/-}$ genotype was confirmed by the following method. A master mix (without DNA) was prepared to provide a volume of 49 µl/sample:

5 µl 10x PCR buffer without MgCl$_2$ (Perkin Elmer)
3.5 µl MgCl$_2$ (Perkin Elmer)
34.5 µl distilled water
1 µl dNTP mix, 10 mM in each of the 4 nucleotides
2.5 µl DMSO
0.5 µl mp 16.1 at 100 µM
0.5 µl mp 16.2 at 100 µM
0.5 µl oligo 801 at 100 µM
0.5 µl oligo 802 at 100 µM
primer sequences:

| mp16.1 5'-ATGATGATGGGCAACGTTC-3' | (SEQ ID no: 6) |
|---|---|
| mp16.2 5'-CAAATATCGCACGATGTC-3' | (SEQ ID no: 7) |
| oligo 801 5'-GGGCGCCCGGTTCTTTT-3' | (SEQ ID no: 8) |
| oligo 802 5'-CCAGCCGGCCACAGTCG-3' | (SEQ ID no: 9) |

0.5 µl Taq polymerase at 1 U/µl
add 1 µl genomic DNA (at 100–500 ng/µl)

Perkin Elmer 9600 thermal cycler was used for the following program:

94° C. for 3 minutes
[94° C./1 minute, 56° C./70 seconds, 72° C./1.5 min] x 35
72° C./5 minutes, 4° C. hold The two primer pairs detect the wildtype (236 bp) and the mutant ("knock-out") allele (510 bp). A 12 μl aliquot was loaded on a 3% agarose gel to visualize and distinguish the band pattern. A 1 kb DNA ladder was run on the gel to provide size standards for comparison. Heterozygotes could be distinguished by the appearance of PCR products of both sizes.

Example 4
Characterization of Eμ-myc/tumor Suppressor Gene Mutation Mouse Strains Eμ-myc/p53$^{+/-}$, Eμ-myc/Rb$^{+/-}$, Eμ-myc/p16$^{+/-}$, and Eμ-myc mice were monitored from birth for development of lymphomas by palpation for enlarged lymph nodes. Results of these experiments are shown in the second column of Table 1. Tumors were analyzed by PCR for retention of wild type tumor suppressor allele. For detection of p53$^+$, the X7, X6.5 and NEO primers were used (see Example 1). Rb and p16 lymphomas were tested for loss of their wild type alleles by the same procedures that were used to confirm the genotype of the progeny of the mouse crosses, as described in Examples 2 and 3, respectively.

Representative results for several Eμ-myc/p53$^{+/-}$ mice tested by the PCR method described in Example 1 are shown in FIG. 3, where the PCR products have been separated by electrophoresis on an agarose gel, according to the size of the DNA fragments. Tumor cell DNA (T in FIG. 3) as template only produced a DNA fragment of the size expected from the mutant allele. "N" indicates tail DNA.

TABLE 1

Tumor Latency and Tumor Suppressor Loss in
Eμ-myc Transgenics Heterozygous for Tumor Suppressor Gene Mutations

| Genotype | Ave. Tumor Latency (days)* | n | Loss of wild-type allele** |
|---|---|---|---|
| Eμ-myc | 113 ± 87 | 46 | Not Applicable |
| Eμ-myc/p53$^{+/-}$ | 27 ± 4.4 | 7 | 4/5 |
| Eμ-myc/Rb$^{+/-}$ | 37 ± 7.8 | 12 | 3/3 |
| Eμ-myc/p16$^{+/-}$ | 31 ± 0.5 | 3 | 2/3 |

*days until palpable tumor detected in inguinal lymph nodes
**tumors analyzed by PCR for retention of wild type tumor suppressor allele in relevant cross (e.g. Eμ-myc/p53$^{+/-}$ animals tested for remaining wild-type p53 allele, etc.)

Example 5
Testing Response to Therapy of Primary myc-induced Lymphomas

Eμ-myc transgenic mice were treated with 10 mg/kg body weight adriamycin (maximum tolerated dose) by intraperitoneal injection using adriamycin freshly resuspended in water to a final concentration of 1 mg/ml. Treated mice were monitored for remission and for relapse by palpation and by blood smears to obtain white blood cell counts.

Palpation is performed by gently feeling the mouse for bumps under the skin, which are enlarged lymph nodes.

Blood smears are done by collecting blood from the tail artery, and examining a dried droplet of blood which has been smeared on a glass microscope slide to be one cell layer thick at the edge. The blood smear is stained after drying, using LEUKOSTAT™ stain (Fisher Diagnostics cat. # CS43A-C). The blood smear can be mounted with Permount™ histological mounting medium (Fisher Scientific). Slides are viewed under 40X or oil emersion. Blood from mice affected by lymphoma are always compared with blood from mice from a normal mouse drawn at the same time.

FIG. 4 shows the time it takes to observe relapse, as assessed by palpation, following a single adriamycin treatment; the vast majority of the mice respond to therapy albeit to a varying degree. The numbers of mice used to generate the data in FIG. 4 were 22 (first treatment), 14 (second treatment) and 5 (third treatment).

Figure 6:
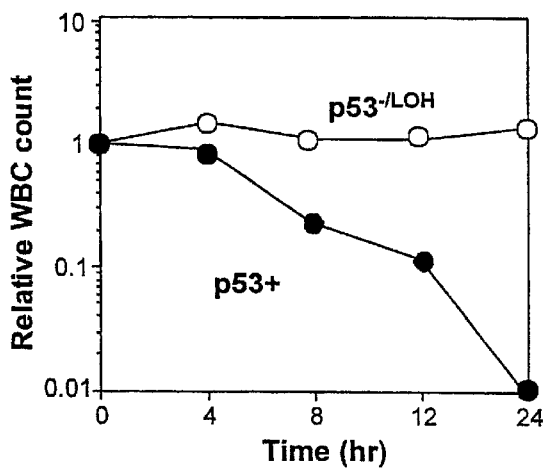
FIG. 6 is a graph showing white blood cell (WBC) counts of Eµ-myc/p53$^{-/-}$ mice compared to white blood cell counts of Eµ-myc/p53$^+$ mice, to monitor the response of lymphoma-associated leukemia to a treatment with 10 mg/kg body weight adriamycin. See Example 6.
Figure 7:
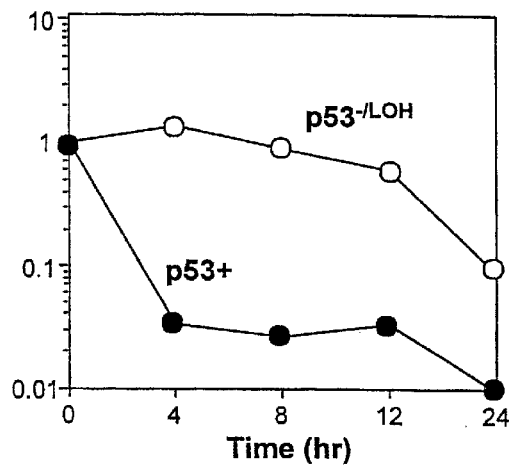
FIG. 7 is a graph showing white blood cell (WBC) counts of Eµ-myc/p53$^{-/-}$ mice compared to white blood cell counts of Eµ-myc/p53$^+$ mice, to monitor the response of lymphoma-associated leukemia to a treatment with 6 Gy total body γ-irradiation. See Example 6.

Eμ-myc/p53$^+$ mice (C57BL/6) and Eμ-myc/p53$^{-/-}$ (C57BL/6 x 129; p53$^{-/LOH}$ in FIGS. 6 and 7) with leukemia associated with primary lymphoma, were treated with either adriamycin at 10 mg/kg of body weight or with 6 Gy of whole body gamma-irradiation. Blood samples were taken and white blood cells were counted in a hemocytometer at 0, 4, 8, 12 and 24 hours after treatment. Results plotted in FIGS. 6 and 7 show that the Eμ-myc/p53$^{-/-}$ lymphoma is insensitive to adriamycin treatment and gamma irradiation. The data plotted in FIGS. 6 and 7 are from one treated mouse of each genotype.

An advantage of animal models is that a large number of tumor samples can be obtained from mice treated identically, where the tumor response is known. These samples will useful for identifying mutations or gene expression changes associated with the drug-resistant state. Tumor materials have been collected to be used for isolation of both DNA and RNA. A summary of the characteristics of drug resistant tumors that have been collected is shown in Table 2.

TABLE 2

| Archived Material | |
|---|---|
| Primary Lymphomas | 32 |
| untreated | 16 |
| de novo resistant | 10 |
| acquired resistant | 6 |
| Matched Primary/Relapse | 11 |
| de novo resistant | 5 |
| acquired resistant | 6 |

Example 6
Tumor Transplantation into Syngeneic Mice

Figure 5:
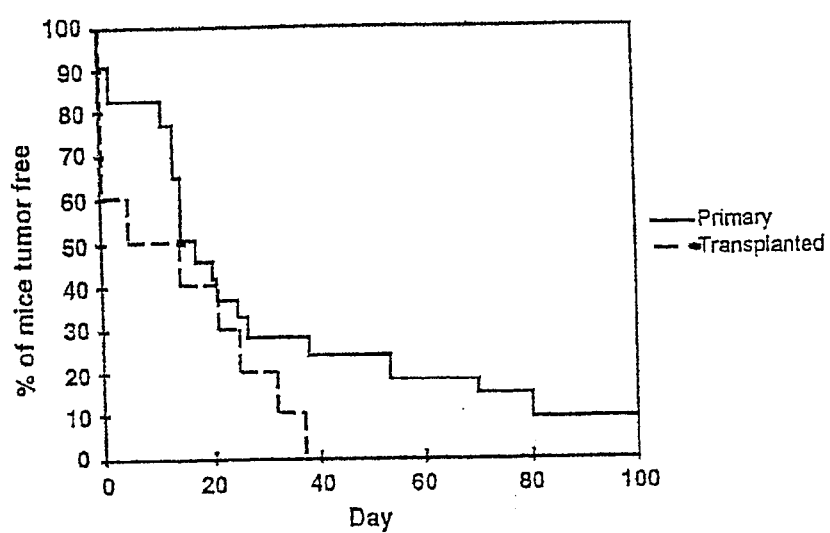
FIG. 5 is a graph showing a comparison between the response to ADR of primary tumors and the response to ADR of transplanted tumors (Protocol 2.

Upon discovery of tumors in a Eμ-myc transgenic mouse, lymphoma cells were harvested, and 10$^6$ cells were immediately transplanted into multiple C57BL/6 mice (Taconic Laboratories) by tail vein injection. Tumors were allowed to form (usually in about two weeks). Treatment with adriamycin was given as in Example 5. A higher percentage of these secondary tumors failed to respond to treatment, but those that did respond behaved similarly to the untransplanted tumors. The results (as assessed by palpation for tumors) plotted in FIG. 5 are from 22 mice with primary tumors, and 10 mice with transplanted tumors.

Example 7
Isolation of Lymphoma Cell Lines from Eμ-myc Mice and from Eμ-myc/Tumor Suppressor Gene Mice Lymphoma cells can be readily cultured using feeder layers (van Lohuizen, M. et al., Cell 65:737–752, 1991). Mice were sacrificed upon appearance of palpable lymph nodes, the lymph nodes were collected into ice cold PBS, and cut open with a scalpel. The cells were filtered through a sterile mesh to remove particulate matter. Lymphocytes were counted in a hemocytometer. Lymphocytes were plated, using $10^6$ cells/ml, on feeder layers in flasks.

For feeder layers, NIH 3T3 cells were plated at subconfluent density in DMEM with 10% calf serum containing 100 units/ml penicillin and streptomycin. When the 3T3 cells reached 50% confluence, they were irradiated with 30 Gy gamma irradiation. Twenty-four hours after irradiation, the cells were trypsinized and reseeded in fresh media at a density of $10^4$ cells/cm$^2$ in 75 cm$^2$ flasks.

Cell lines produced from Eμ-myc/p53$^{+/-}$ mice (Example 1) were tested for their genotype using PCR (Example 1), and found to be Eμ-myc/p53$^{-/-}$. Cell lines have been assigned identification numbers: L876, L877, L1515, L1522, L1537, L1542, L1570, L1575, L1624, L1625, L1715, L1726, L1731 and 1736.

Cell lines produced from Eμ-myc/Rb$^{+/-}$ mice (Example 2) were tested to identify their Rb alleles using PCR (Example 2), and were found to be Eμ-myc/Rb$^{+/-}$.

Cell lines produced from Eμ-myc/p16$^{+/-}$ mice (Example 3) were tested to identify their p16 alleles, using PCR (Example 3), and were found to be Eμ-myc/p16$^{-/-}$. L1213 and L1305 are two such cell lines.

Several lymphoma lines have been isolated from Eμ-myc mice in which the response to adriamycin of the original tumor was known. Eμ-myc lymphoma cell lines cultured in vitro were tested for their sensitivity to adriamycin. Lymphocytes were counted. The cells were spun down and resuspended in pre-conditioned B cell media (media that has been on feeder cells for 24 hours) at a concentration of $2\times10^6$ cells/ml. $10^6$ cells were seeded per well of a tissue culture plate, in 0.5 ml. Adriamycin was suspended in pre-conditioned B cell media at twice the final concentration. Final concentrations of adriamycin were 0.25, 0.05, 0.075, 0.1, 0.5 and 1.0 μg/ml. 0.5 of medium was added to each well, to a final volume of 1 ml. Cells were incubated for 24 hours at 37° C. Cells were transferred from the wells to Eppendorf tubes on ice, and centrifuged at 2500 rpm for 5 minutes at 4° C. The medium was poured off the cell pellets, leaving about 200 μl of medium in each tube. One drop of trypan blue dye was added to each tube, and a total of 200 cells per sample were counted under a microscope. Live cells exclude trypan blue and appear white; dead cells take up trypan blue and appear blue.

Figure 8:
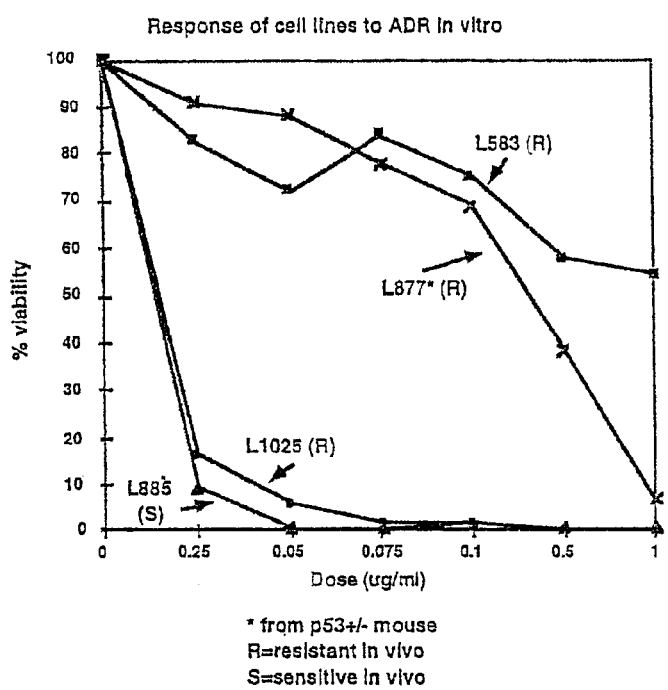
FIG. 8 is a graph illustrating the response of cell lines to adriamycin in vitro. The viability of the cells (percent) is plotted against the dose (in µg/ml) of adriamycin given to the cells. Responses are shown for four different lymphoma cell lines. See Example 7.

FIG. 8 shows adriamycin dose response curves for four different lymphoma cell lines (L583, L877, L1025 and L885), showing the percent viable cells in a sample of the cells following a 24-hour treatment with adriamycin at the concentration shown on the ordinate. L877 has been tested as Eμ-myc/p53$^{-/-}$; the other cell lines are derived from Eμ-myc/p53$^+$ mice and are presumably p53$^{+/+}$.

Some resistant tumors were sensitive in cell culture (e.g., line L1025), implying that in vitro studies alone are insufficient for a complete understanding of factors involved in drug cytotoxicity.

Example 8

Detection of Chromatin Condensation and Poly-ADP Ribose Polymerase Cleavage in Isolated Tumor Cells from Primary Tumors of Eμ-myc Mice (p53+)

Eμ-myc mice with palpable tumors were treated with adriamycin at 10 mg/kg body weight. Eight hours after treatment, lymph nodes were excised and tumor cells isolated as in Example 7. Isolated tumor cells were placed on ice and either fixed and stained with DAPI or lysed for PARP [poly(ADP-ribose) polymerase] western blot analysis.

To observe nuclear apoptotic changes, nuclei were fixed with 4% paraformaldehyde, stained with DAPI (4', 6-diamidino-2-phenylindole; 1 mg/ml) and examined by fluorescence microscopy using a UV filter. Apoptotic cells display a characteristic condensation of chromatin and often, nuclear fragmentation. The percentage of cells undergoing apoptosis is determined by counting the percentage of cells with condensed DNA.

Figure 9:
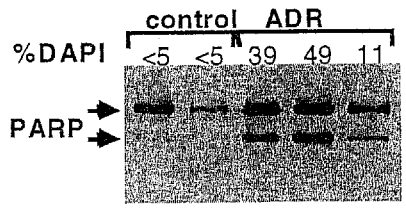
FIG. 9 is a photograph of a Western blot of a polyacrylamide gel resulting from electrophoresis of isolated lymphoma cell lysates, tested for poly-ADP ribose polymerase (PARP) cleavage. The proportion of cells with condensed DNA (staining with DAPI) is given for a sample of each cell lysate, as a measure of the proportion of cells undergoing apoptosis. See Example 9.

Cleavage of poly (ADP-ribose) polymerase is a common event in apoptosis. (See Kaufmann, S. H., Desnoyers, S., Ottaviano, Y., Davidson, N. E., and Poirier, G. G., 1993. Specific proteolytic cleavage of poly(ADP-ribose) polymerase: an early marker of chemotherapy-induced apoptosis. *Cancer Res* 53, 3976–85.) $2\times10^6$ cells were washed with PBS, pelleted and frozen at −70° C. Cells were lysed in NP-40% lysis buffer (1% NP-40; 150 mM NaCl; 50 mM Tris-HCl, pH 8.0; 1 mM sodium vanadate) supplemented with protease inhibitor cocktail (0.1 mM PMSF, 10 μg/ml cytochalasin B and 2 μg/ml of chymostatin, leupeptin, antipain and pepstatin) for 60 min on ice. Lysates were centrifuged at 10,000 rpm for 5 min at 4° C. and protein concentration was estimated by the Bio-Rad Protein Assay using BSA as the standard. Thirty μg of total protein were loaded onto a 10% SDS-polyacrylamide gel, separated by electrophoresis, and transferred to an Immobilon-P membrane (Millipore). Western blot analysis was carried out according to standard procedures using ECL detection. PARP antibody (Santa Cruz or Upstate Biotechnology) and the secondary antibody, horseradish peroxidase-conjugated sheep anti-mouse, were both used at a 1:1000 dilution. Results are shown in FIG. 9.

Example 9

Figure 10:
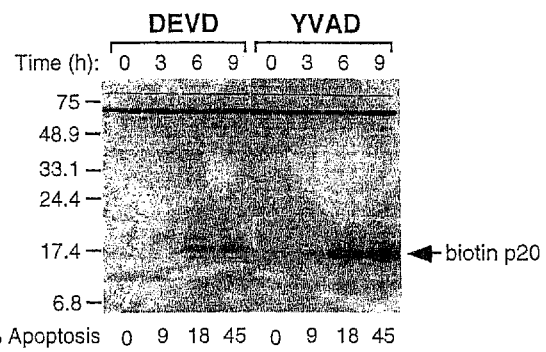
FIG. 10 is a photograph showing isolated lymphoma cell extracts run on an SDS-polyacrylamide gel, blotted against biotinylated tetrapeptide inhibitors that irreversibly bind to activated caspases (biotin YVAD-AMK and biotin-DEVD-CMK; Faleiro, L., et al., *EMBO J.* 16:2271–2281, 1997), for the detection of caspase activation, a biochemical hallmark of apoptosis. See Example 9.

Detection of Caspase Activation in L700 Cell Line Derived from an Eμ-myc (p53$^+$) Tumor Procedures were as published in Faleiro, L., et al., *EMBO J.* 16:2271–2281, 1997). Isolated L700 cells growing in culture dishes were treated with 0.1 μg/ml adriamycin. After 0, 3, 6 or 9 hours, cell lysates were made in the presence of 10 μM biotin-YVAD-amk to label caspases, and the protein concentrations were determined. Protein samples were run on a 15% acrylamide-0.1% SDS gel. Proteins were transferred from the gel to Immobilon P membrane (Millipore). Membranes were washed in methanol and air dried. Dried, baked membranes were incubated in biotinylated horseradish peroxidase at 25 ng/ml. Labeled proteins were visualized with ECL reagent (Amersham). FIG. 10 shows caspase activation following drug treatment.

Example 10

Assessment of Drug Sensitivity in Transplanted Tumor Cells

Figure 11:
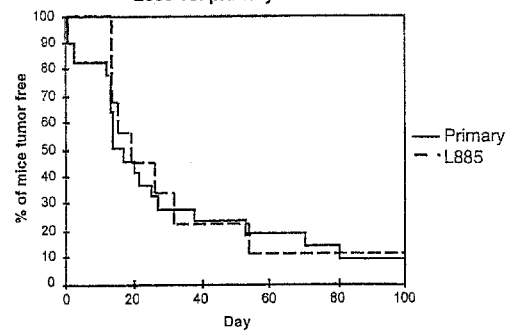
FIG. 11 is a graph showing the response of L885 cells or primary tumors to adriamycin. The percentage of tumor-free mice is plotted against the number of days after adriamycin treatment. The response of primary tumors is shown with a solid line; the response of the L885 cell line is shown with a broken line. See Example 10.

Eμ-myc lymphomas were cultured using feeder layers (see Example 7). Several of these cell lines were transplanted into syngeneic C57BL/6 recipients by injection of $10^6$ cells into the tail vein. Tumor-bearing animals were assessed for response to 10 mg/kg adriamycin therapy, by palpation for tumors. FIG. 11 shows the response of 9 secondary tumors arising from transplanted L885 cells, and the response of 22 primary, non-transplanted tumors. The response of cell line L885 was virtually indistinguishable from that seen in the primary, non-transplanted lymphomas.

Tumor cell line L1537 was derived from an Eμ-myc/p53$^{+/-}$ lymphoma and was tested as homozygous for p53$^-$. Tumor cells were transplanted, by the method described above, into two C57BL/6 mice. Both mice failed to respond to adriamycin therapy.

Example 11

Infection of L885 Cells with Recombinant Retroviral Vectors

To determine whether L885 cells can be infected with recombinant retroviral vectors, a green fluorescent protein (GFP)-expressing retrovirus was generated using the Phoenix packaging cell line (provided by G. Nolan, Stanford University). Other viral packaging systems are available for similar applications. BOSC 23 cells can also be used, for example (David Baltimore, California Institute of Technology).

Phoenix cells prior to passage 20 were plated at 5.5 x 10$^6$ cells/10 cm diameter plates in 10 ml of media 12–24 hours before transfection. Fresh media containing 25 μM choroquine was added just before transfection. 20 μg DNA was mixed with 62.5 μl of 2 M CaCl$_2$ in a total volume of 500 μl water. This mixture was added to 500 μl of HBS (HBS is 280 mM NaCl, 10 mM KCl, 1.5 mM Na$_2$HPO$_4$-2H$_2$O, 2 mM dextrose, 50 mM HEPES, pH 7.05) dropwise while agitating the HBS with air bubbles. The resulting mixture was allowed to precipitate for 5–10 minutes. The solution was then added to the cells and the cells were incubated. After 10–12 hours, the cell media was changed to stop transfection. Virus was collected for 36 hours. Twelve hours before infection (24 hours after transfection), the cell media was changed to B-cell media.

Twenty-four hours before infection, the lymphoma cells (L885 cells) were plated at 5×10$^6$ on fresh feeder layers. For infection, the lymphoma cells were collected and centrifuged at 1500 rpm for 5 minutes. Old media was removed. Media from the Phoenix cells was collected in a 10 cc syringe, 4 μg/ml polybreen was added, and the mixture was filtered through a 0.45 μm filter onto the lymphoma cells. The lymphoma cells were put back on feeder cells (in 10 cm plates) and centrifuged for 30 minutes at 1500 rpm. They were then incubated for 8–12 hours. New B cell 9: medium was added to the Phoenix cells and they were incubated for another 8–12 hours.

Figure 12:
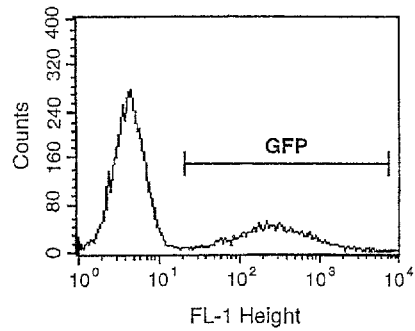
FIG. 12 is a graph showing flow cytometry analysis for green fluorescent protein (GFP) expression in L885 cells that have been infected with recombinant retrovirus expressing GFP using the Phoenix packaging line. See Example 11.

The lymphoma cells were infected a second time as above. Twelve hours after the second infection, the lymphoma cells were spun down as before, and the medium containing polybreen removed. Fresh B cell medium was added. Twelve to 23 hours after infection, infected cells were selected by addition of 2 μg/ml puromycin, sorted by FACS (fluorescence activated cell sorting) for GFP positive cells, or other selection (hygromycin, neomycin, etc.) FIG. 12 shows flow cytometry analysis for GFP expression. L885 lymphoma cells are readily infectible using this procedure.

Example 12

Effect of p53 Defect on Therapy in Eμ-myc p53$^{+/-}$ Mice

Figure 13:
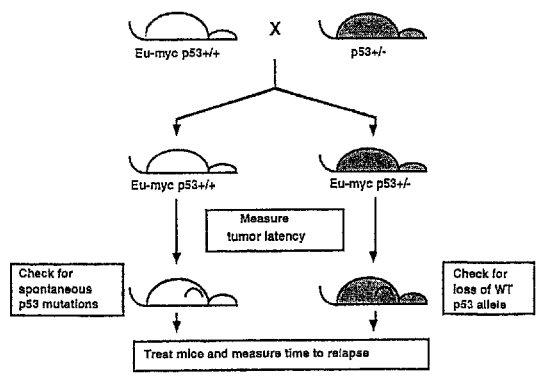
FIG. 13 is a diagram showing a scheme to study the response of essentially p53-deficient tumors in mice that are otherwise hemizygous for p53 and not prone to thymic lymphoma. See Example 12.
Figure 14:
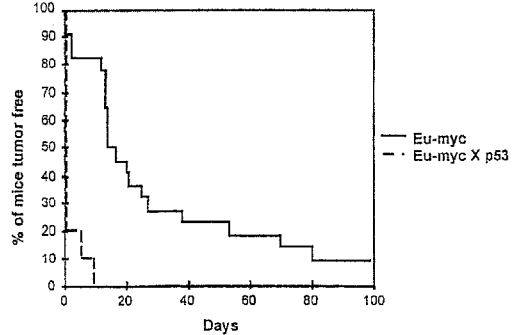
FIG. 14 is a graph showing the in vivo response to adriamycin of Eµ-myc or Eµ-myc/p53$^{+/-}$ mice, as the percentage of tumor-free mice against the days after adriamycin treatment. See Example 12.

To determine the impact of reduced p53 dosage on lymphoma therapy, we generated Eμ-myc transgenic mice in a p53$^{+/-}$ (heterozygous) background (Example 1). p53$^{-/-}$ mice typically die from thymic lymphoma by 4.5 months, whereas the p53$^{+/-}$ mice do not develop tumors until approximately 18 months and with few lymphomas (Donehower, L. A. et al. Semin. Cancer Biol., 7:269–278 (1996)). Since most Eμ-myc lymphomas from p53$^{+/-}$ mice lose the wild-type p53 allele, it was possible to study the response of essentially p53-deficient tumors in mice that were otherwise hemizygous for p53 and not prone to thymic lymphoma (see strategy in FIG. 13). The response of 10 Eμ-myc/p53$^{+/-}$ mice to adriamycin therapy is shown in FIG. 14. As in human lymphomas with p53 defects, Eμ-myc lymphomas from p53$^{+/-}$ mice were almost completely refractory to therapy. The response of Eμ-myc lymphomas with p53 defects to 10 mg/kg adriamycin therapy resembled that of Eμ-myc/p53$^{+/+}$ lymphomas following their second relapse (See FIG. 4).

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A transgenic mouse having a genome comprising a myc gene operably linked to an Eµ IgH enhancer and further comprising one inactivated p16 allele, wherein said mouse exhibits accelerated development of lymphomas compared to Eµ-myc mice.

2. A lymphoma cell line produced from primary lymphoma cells isolated from the transgenic mouse of claim 1.

3. A method for assessing an effect of a gene on the response of a lymphoma to a treatment, said method comprising the steps of:
    a) producing a cell line from the lymphoma;
    b) introducing a gene into a population of cells of the cell line, thereby producing altered cells of the cell line;
    c) introducing altered and unaltered cells of the cell line into different recipient mice, thereby producing test recipient mice and control recipient mice, respectively;
    d) allowing lymphomas to arise in the test recipient mice and the control recipient mice, thereby producing lymphoma-containing test recipient mice and lymphoma-containing control recipient mice;
    e) administering the treatment to the lymphoma-containing test recipient mice of step d) and the lymphoma-containing control recipient mice of step d); and
    f) monitoring the lymphoma-containing test recipient mice of step e) and the lymphoma-containing control recipient mice of step e) for remission of lymphomas;
wherein a difference in the frequency of remissions in the test recipient mice compared to the frequency of remissions in the control recipient mice indicates an effect of the gene on the response of the lymphoma to the treatment.

4. The method of claim 3 wherein the lymphoma is from a transgenic mouse having a genome comprising a myc gene operably linked to an Eµ IgH enhancer and further comprising one inactivated p53 allele.

5. The method of claim 3 wherein the lymphoma is from a transgenic mouse having a genome comprising a myc gene operably linked to an Eµ IgH enhancer and further comprising one inactivated Rb allele, wherein said mouse develops lymphomas.

6. The method of claim 3 wherein the lymphoma is from a transgenic mouse having a genome comprising a myc gene operably linked to an Eµ IgH enhancer and further comprising one inactivated p16 allele, wherein said mouse exhibits accelerated development of lymphomas compared to Eµ-myc mice.

7. A method for testing a lymphoma for sensitivity to a treatment in a transgenic mouse having a genome comprising a myc gene operably linked to an Eµ IgH enhancer and further comprising one inactivated p16 allele, wherein said mouse exhibits accelerated development of lymphomas compared to Eµ-myc mice, comprising administering said treatment to the mouse and monitoring the mouse for remission of the lymphoma, wherein remission of the lymphoma indicates sensitivity to the treatment, and sensitivity of the lymphoma to the treatment is proportional to the length of time until relapse.

8. A method for testing a lymphoma for sensitivity to a treatment, comprising administering said treatment in vitro to lymphoma cells derived from a transgenic mouse having a genome comprising a myc gene operably linked to an Eµ IgH enhancer and further comprising one inactivated p16 allele, wherein said mouse exhibits accelerated development of lymphomas compared to Eµ-myc mice, and monitoring the cells for growth, wherein slowing or arresting of growth indicates sensitivity of the lymphoma to said treatment.

9. A method for testing lymphomas for sensitivity to a treatment, comprising harvesting lymphoma cells from a transgenic mouse having a genome comprising a myc gene operably linked to an Eµ IgH enhancer and further comprising one inactivated p16 allele, wherein said mouse exhibits accelerated development of lymphomas compared to Eµ-myc mice, transplanting the cells into recipient mice, allowing lymphomas to arise in the recipient mice, administering the treatment to the recipient mice, thereby producing treated recipient mice, and monitoring the treated recipient mice for remission of the lymphomas, wherein more frequent remissions among treated recipient mice compared to untreated recipient mice indicates sensitivity of the lymphomas to the treatment.

10. A method for identifying a treatment which reduces the extent to which lymphoma occurs, comprising administering a treatment to a transgenic mouse having a genome comprising a myc gene operably linked to an Eµ IgH enhancer and further comprising one inactivated p16 allele, wherein said mouse exhibits accelerated development of lymphomas compared to Eµ-myc mice, which mouse, referred to as a test mouse after treatment, develops lymphomas, assessing the extent to which lymphoma is present in the test mouse after the treatment, and comparing the extent to which lymphoma is present in the test mouse after treatment with the extent to which the lymphoma is present in an appropriate control mouse, wherein if the lymphoma is present to a lesser extent in the test mouse than in the control mouse, the treatment reduces the extent to which lymphoma occurs.

\* \* \* \* \*